United States Patent [19]
Lesiczka et al.

[11] Patent Number: 5,716,572
[45] Date of Patent: Feb. 10, 1998

[54] FLASHLESS CATHETER BEVELING PROCESS

[75] Inventors: Peter H. Lesiczka, Middletown; Julien C. Mathieu, Avon, both of Conn.

[73] Assignee: Johnson & Johnson Medical, Inc., Arlington, Tex.

[21] Appl. No.: 707,592

[22] Filed: Sep. 5, 1996

[51] Int. Cl.[6] ............................... B29C 37/02; B28B 7/14
[52] U.S. Cl. ..................... 264/161; 264/163; 264/296; 264/320; 264/322; 264/DIG. 66; 425/292; 425/393; 425/806
[58] Field of Search ..................... 264/161, 163, 264/320, 296, 500, DIG. 66, 322, 150; 425/393, 292, 298, 302.1, 806

[56] References Cited

U.S. PATENT DOCUMENTS

| | | |
|---|---|---|
| 3,539,674 | 11/1970 | Dereniuk et al. . |
| 3,843,300 | 10/1974 | Mc Farlane . |
| 3,929,959 | 12/1975 | Findlay et al. .................. 264/292 |
| 3,929,960 | 12/1975 | Findlay et al. .................. 264/292 |
| 3,983,203 | 9/1976 | Corbett .......................... 264/296 |
| 4,177,237 | 12/1979 | Ueno et al. ..................... 264/296 |
| 4,264,294 | 4/1981 | Ruiz . |
| 4,292,270 | 9/1981 | Hannah et al. .................. 264/296 |
| 4,373,894 | 2/1983 | Peppel ........................... 264/296 |
| 4,404,159 | 9/1983 | McFarlane . |
| 4,551,292 | 11/1985 | Fletcher et al. ................. 264/322 |
| 4,661,300 | 4/1987 | Daugherty . |
| 4,904,433 | 2/1990 | Williamitis . |
| 4,961,809 | 10/1990 | Martin ........................... 264/322 |
| 5,102,324 | 4/1992 | Bullard et al. . |
| 5,209,882 | 5/1993 | Hattori et al. ................... 264/296 |
| 5,397,512 | 3/1995 | Sloane, Jr. et al. . |
| 5,409,644 | 4/1995 | Martin et al. ................... 264/296 |
| 5,425,903 | 6/1995 | Sloane, Jr. et al. ............. 264/22 |

*Primary Examiner*—Jan H. Silbaugh
*Assistant Examiner*—Mark Eashoo

[57] ABSTRACT

A flashless catheter beveling process in which a beveling catheter mold has an internal cavity which defines the external beveled shape of the catheter and also has a circular hole centrally located therein. In the beveling mold, one end of a distal endmost interior bevel terminates at the surface of the beveling mold, with the distal endmost bevel and the surface forming an angle at the edge of the circular hole. A cylindrical support pin is inserted into a hollow extruded unbeveled catheter tube. The beveling mold is heated and positioned relative to and around the extruded catheter tube with the cylindrical support pin positioned in the circular hole of the mold. This arrangement melts the extruded catheter tube to allow it to flow within and assume the shape defined by the internal cavity of the beveling mold, and the molten catheter material flashes through a narrow annular gap defined between the cylindrical support pin and the circular hole. The cylindrical support pin is then withdrawn from the circular hole in the beveling mold, and one end of a cone pin is positioned in contact with the circular hole. The cone pin contacts the circular edge formed by the surface of the mold and the distal endmost bevel, and pinches off the flash which has been extruded through the annular gap. The molded catheter is then removed from the catheter mold, and the cylindrical support pin is withdrawn from the finished and molded catheter.

13 Claims, 7 Drawing Sheets

FLASHLESS CATHETER BEVELING PROCESS

BACKGROUND OF THE INVENTION

1. Field of the Invention

The present invention relates generally to a flashless catheter beveling process, and more particularly pertains to a catheter beveling process for forming catheter bevels which are geometrically identical and without any resultant flash.

The present invention relates to a method for flashless beveling of an intravenous (IV) catheter, and more particularly pertains to a method for forming a beveled tip on a thin walled catheter constructed of a plastic material such as polyurethane or Teflon®.

Intravenous catheters are particularly used in medical applications for introducing blood, plasma, or other fluids into the circulatory system of a patient. While IV catheters are available in several different types, one common type of catheter is constructed so as to be mounted upon a relatively long, hollow cannula (needle) with a slight frictional fit. A hub is attached to one end of the catheter and is designed so as to be connectable with and detachable from an IV fluid supply line. To insert the catheter into the patient, the cannula and catheter together are inserted through the patient's skin into a vein, and thereafter the cannula can be withdrawn, leaving the catheter in place therein.

As manufactured, catheters have distal ends which are those ends to be inserted through the skin of a patient. The use of a catheter with a blunt distal or leading end is not desirable since the blunt tip tends to resist insertion into the skin, thereby increasing the difficulty and trauma of the insertion. Moreover, insertion of a blunt tip increases the irritation to the surrounding tissue, and perhaps more importantly, adds significantly to the pain and discomfort of the patient during insertion.

Consequently, in the prior art the tips on IV catheters have been tapered or beveled to eliminate the aforementioned problems. The methods for providing such a beveled tip, however, are relatively few and often not publicly disclosed. Moreover, polyurethane catheters are particularly difficult to form, and thus there are relatively few known methods whereby a beveled tip can be formed on a polyurethane catheter.

Accordingly, a method for beveling an IV catheter is desirable which provides a uniform beveled tip, and is sufficiently fast and simple so as to permit beveling of catheters in large quantities.

2. Discussion of the Prior Art

In the prior art, catheters with bevels have been produced by molding a catheter in a catheter beveling mold defining the beveled shape of the catheter and having a through pin projecting therethrough. The basic beveled shape of the catheter is then molded in the catheter beveling mold by heating a polymeric tubing to allow it to deform and flow freely throughout the mold and define the basic bevel geometry of the catheter.

However, in the prior art, the upper end of the 27° bevel did not end or terminate at the upper surface of the beveling mold. Instead, the upper end of the 27° bevel terminated approximately 0.020 inches below the upper surface of the beveling mold, with the upper 0.020 inches of the mold defining the shape of a hollow cylindrical land. During commercial operation, the process controls were such that in some instances the molten polymer did not completely fill the 27° bevel volume (a short shot), and in other instances the molten polymer extruded beyond the 27° bevel volume into the 0.020 inch hollow cylindrical land. The molded part was then considered to be finished in the condition as molded, and vision inspection systems would reject parts with excessive flash or insufficiently filled parts.

SUMMARY OF THE INVENTION

Accordingly, it is a primary object of the present invention to provide a catheter beveling process which forms catheter bevels that are geometrically identical and without any resultant flash.

A further object of the subject invention is the provision of a catheter beveling process which allows polymeric tubing to flow freely when heated to define the basic bevel geometry. This makes beveling much easier than prior art beveling processes, because it makes the process much more robust with respect to the tolerances for process parameters, and also can reduce total beveling time. More importantly, it allows exact and clean removal of the process flash.

Pursuant to the catheter beveling process of the present invention, in the beveling mold the upper end of the distal endmost bevel (27° bevel) terminates at the upper surface of the beveling mold, with the distal endmost bevel and the upper surface of the beveling mold forming an acute angle and a relatively sharp circular edge. Accordingly, when a cone pin is lowered onto and contacts the beveling mold, the beveled lower end of the cone pin contacts the relatively sharp circular edge formed by the upper surface of the mold and the distal endmost bevel, and is very effective in pinching off and completely removing the extrudate flash.

In accordance with the teachings herein, the present invention provides a flashless catheter beveling process in which a beveling catheter mold has an internal cavity which defines the external beveled shape of the catheter and also has a circular hole centrally located therein. In the beveling mold, one end of a distal endmost interior bevel terminates at the surface of the beveling mold, with the distal endmost bevel and the surface forming an angle at the edge of the circular hole. A cylindrical support pin is inserted into a hollow extruded catheter tube. The beveling mold is heated and positioned relative to and around the extruded catheter tube with the cylindrical support pin positioned in the circular hole of the mold. This arrangement melts the extruded catheter tube to allow it to flow within and assume the shape defined by the internal cavity of the beveling mold, and the molten catheter material flashes through a narrow annular gap defined between the cylindrical support pin and the circular hole. The cylindrical support pin is then withdrawn from the circular hole in the beveling mold, and one end of a cone pin is positioned in contact with the circular hole. The cone pin contacts the circular edge formed by the surface of the mold and the distal endmost bevel, and pinches off the extrudate flash which has been extruded through the narrow annular gap. The catheter mold is then removed from the molded catheter, and the cylindrical support pin is withdrawn from within the finished and molded catheter.

In greater detail, the distal endmost bevel and the surface of the beveling mold form an acute angle and a relatively sharp circular edge. Moreover, the cylindrical support pin is initially inserted into the hollow catheter tube to project a distance beyond the end of the hollow extruded catheter tube, and is later withdrawn until it is positioned just below the surface of the beveling mold.

The beveling mold is heated by being positioned within and contacting a temperature controlled heater block, and the cone pin extends through an aperture in the temperature controlled heater block. The temperature controlled heater block includes an internal frustoconical cavity having the same general shape as an external frustoconical surface of the beveling mold to maximize the heat flow therebetween.

The distal endmost bevel extends at a bevel angle of substantially 27° with respect to the longitudinal axis of the mold and the molded catheter. The beveling catheter mold further defines a second interior bevel extending at a bevel angle of substantially 3° with respect to the longitudinal axis of the mold and the molded catheter.

After molding the beveled catheter, the beveling catheter mold is cooled by a flow of air directed across the mold, and the cooling air also blows away the pinched off extrudate. In one embodiment, the cylindrical support pin is hollow and after molding the beveled catheter, a cooling flow of compressed air is directed through the hollow cylindrical support pin.

During the flashless catheter beveling process, the beveling mold is removed downwardly by a servo control system at an initial fast rate onto the extruded catheter tube until a shallow tapered portion of the mold begins to contact the extruded hollow catheter tube. Thereafter, the servo system lowers the heated mold downwardly onto the extruded catheter tube at a slower, controlled approach rate, melting the exterior surface of the extruded catheter tube to allow it to flow within and assume the shape defined by the interior cavity of the beveling mold. The downward travel of the heated catheter mold is stopped by the servo control system as the molten catheter material flashes through the narrow annular gap.

BRIEF DESCRIPTION OF THE DRAWINGS

The foregoing objects and advantages of the present invention for a flashless catheter beveling process may be more readily understood by one skilled in the art with reference being had to the following detailed description of several preferred embodiments thereof, taken in conjunction with the accompanying drawings wherein like elements are designated by identical reference numerals throughout the several views, and in which.

DETAILED DESCRIPTION OF THE DRAWINGS

Figure 1:
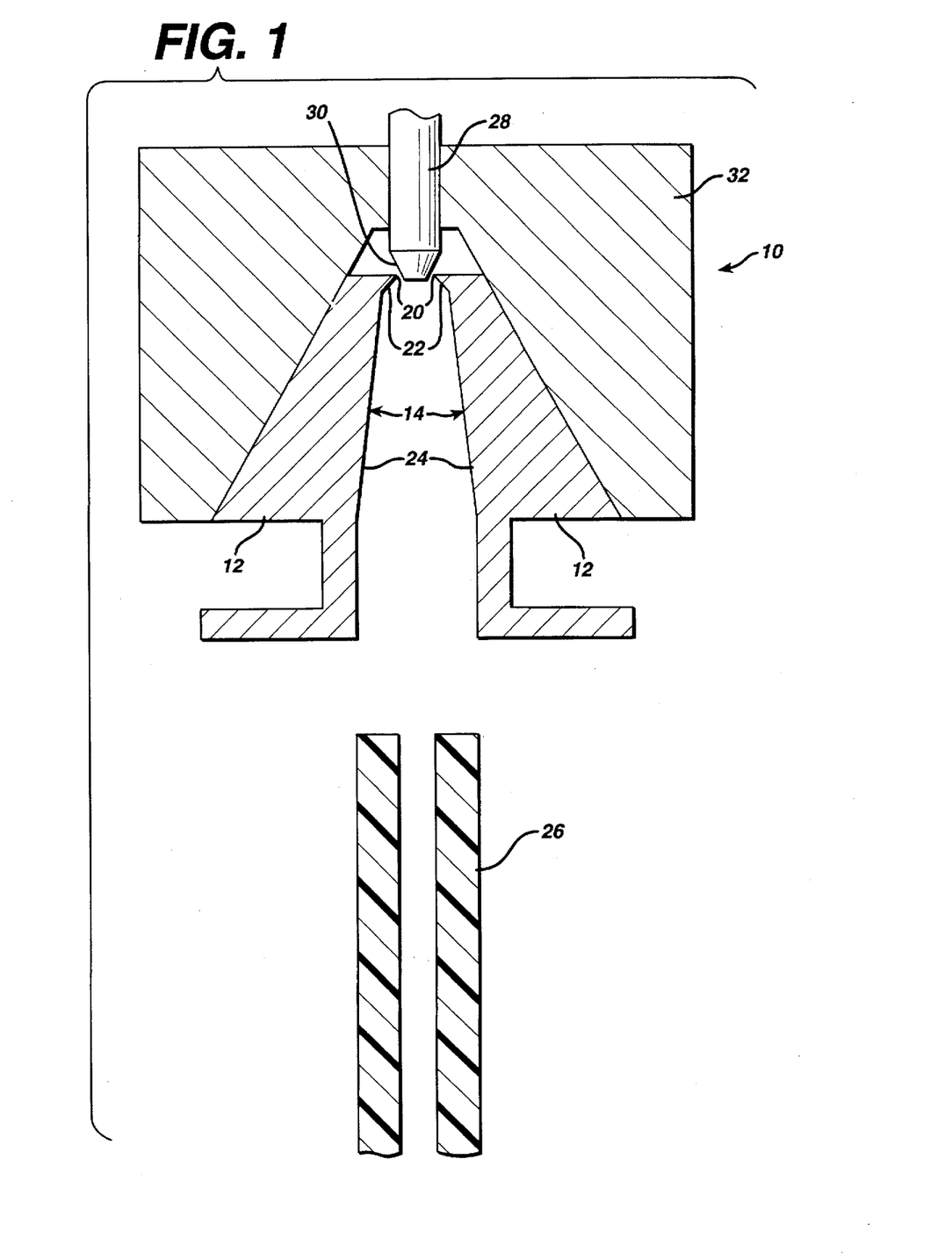
FIG. 1 illustrates the first step of the flashless catheter beveling process of the present invention in which a beveling mold which defines the external shape of the catheter is positioned within to contact and be heated by a temperature controlled heater block, a cylindrical cone pin with a frustoconical tapered bottom tip extends through a top aperture in the temperature controlled heater block, and an extruded hollow catheter tube is positioned centrally below the beveling mold.
Figure 2:
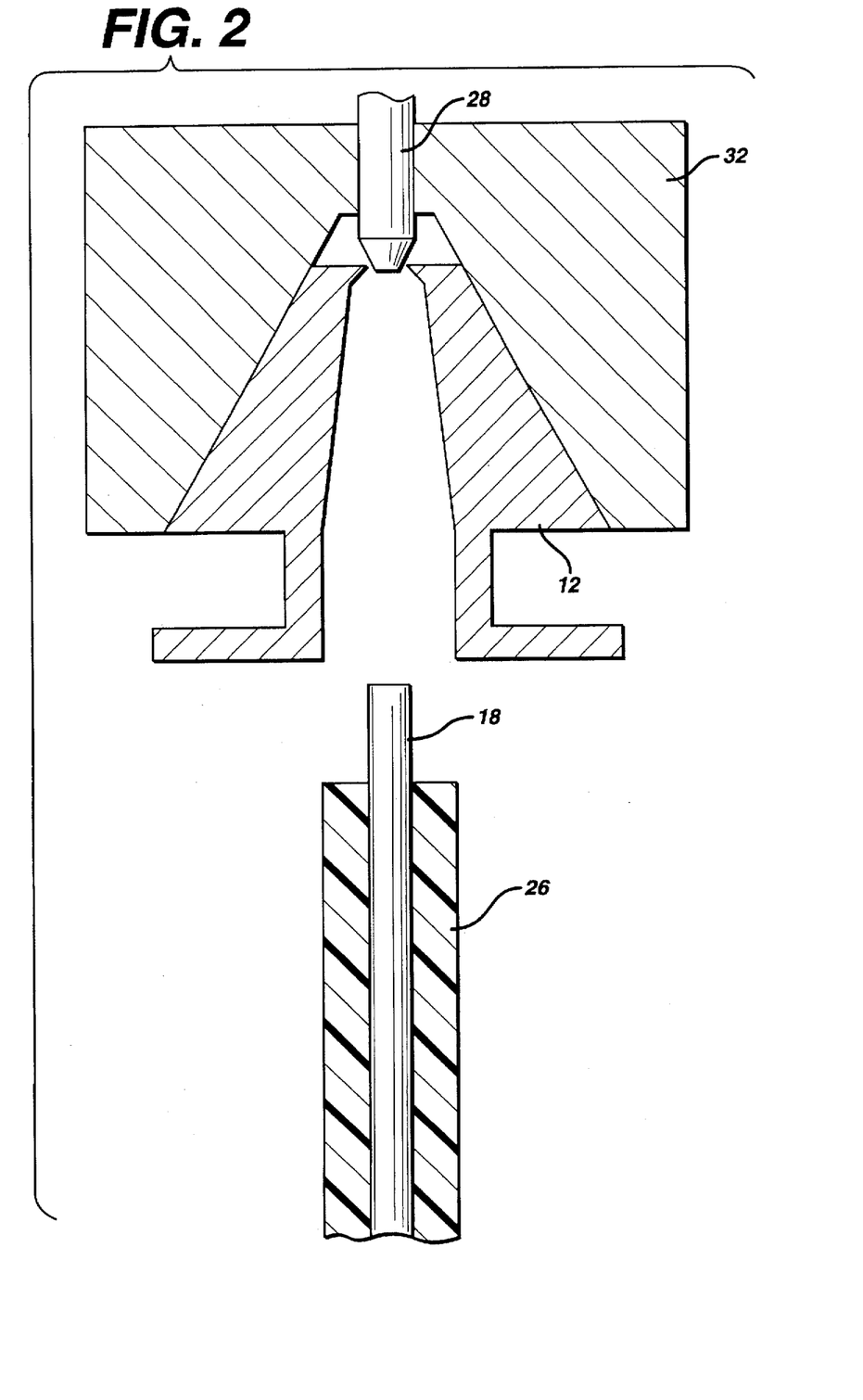
FIG. 2 illustrates the second step of the flashless catheter beveling process in which a cylindrical support pin is inserted into the hollow extruded catheter tube.
Figure 7:
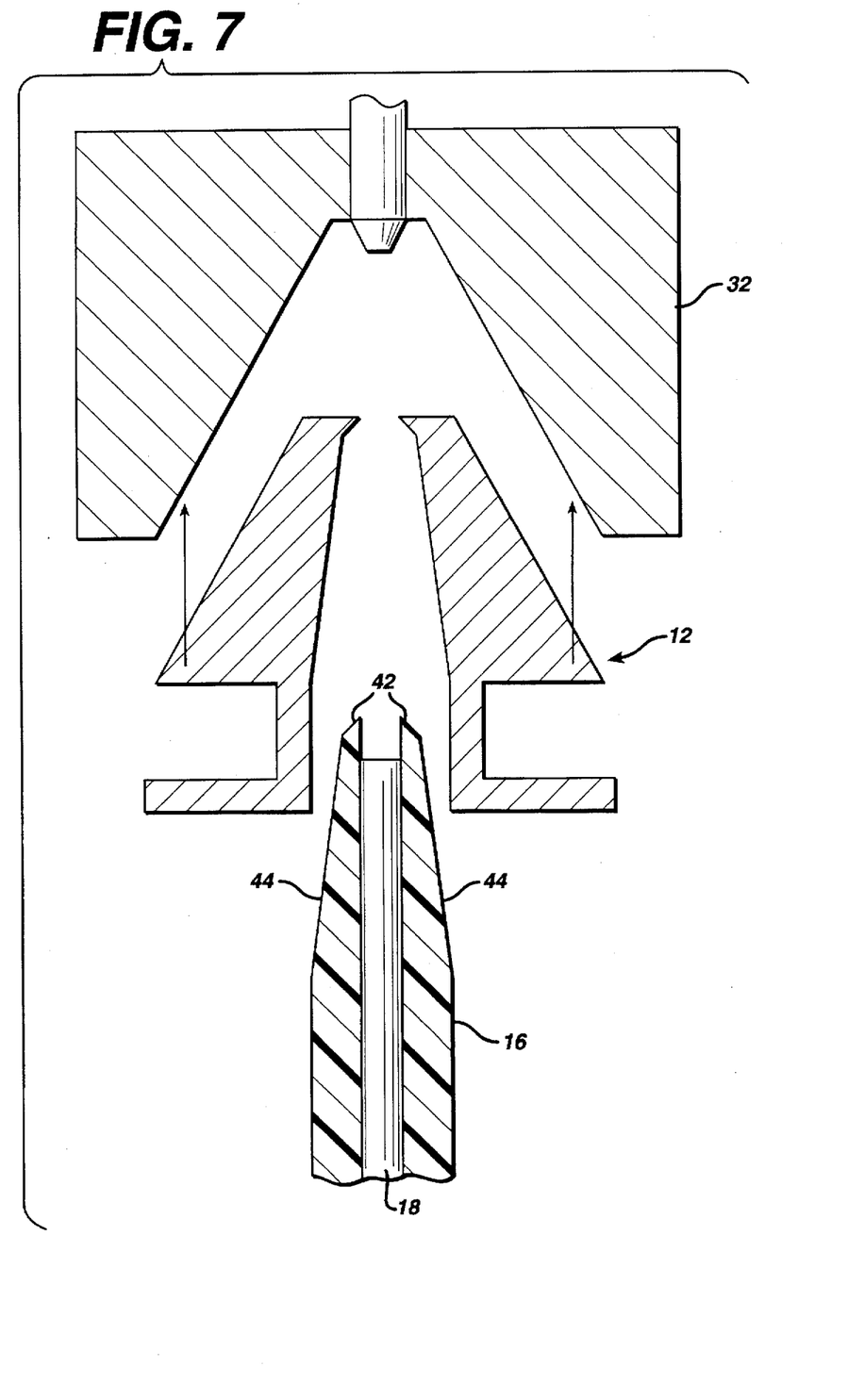
FIG. 7 illustrates the seventh step of the flashless catheter beveling process in which the catheter mold is raised back into contact with the temperature controlled heater block to be reheated for the next cycle of operation, and the cylindrical support pin is withdrawn downwardly from within the finished and molded catheter.

Referring to the drawings in detail, FIG. 1 illustrates a molding arrangement 10 which includes a heated beveling mold 12, the interior shape 14 of which defines the overall exterior beveled shape of a molded catheter 16, which is shown in FIG. 7. As illustrated in FIG. 2, an extruded polymeric tubing to be molded into a beveled catheter is supported on a support through pin 18. The support pin 18 is inserted into the beveling mold 12 from the bottom thereof and projects through the mold and extends into and through a circular aperture 20 in the top of the mold 12. The beveling mold 12 defines a first interior beveled shoulder 22 extending at a bevel angle of substantially 27° with respect to the longitudinal axis of the mold 12 and the molded catheter 16, and further defines a second interior beveled shoulder 24 extending at a shallow bevel angle of substantially 3° with respect to the longitudinal axis of the mold 12 and the molded catheter 16.

The extruded polymeric tubing 26 is fed into the mold supported on the through pin 18, and is melted by the heated exterior beveling mold 12 to conform to the interior shape of the beveling mold. Some of the plastic melt will flow between the support pin 18 and the aperture 20 to form an extrudite flash thereat. The support pin 18 is then withdrawn from the circular aperture in the mold, and a cone pin 28 having a beveled or tapered bottom tip 30 is lowered from above to pinch off the extruded flash.

FIG. 1 illustrates the first step of the flashless catheter beveling process in which the beveling mold 12, which defines the desired external beveled shape of the catheter, is positioned within, to contact and be heated by, a temperature controlled heater block 32. The temperature controlled heater block 32 includes an internal frustoconical cavity 34 having the same general shape as the external frustoconical surface 36 of the beveling mold 12 to maximize the heat flow therebetween. A cylindrical cone pin 28 with a frustoconical tapered bottom tip 30 also extends through a central aperture in the temperature controlled heater block. An extruded hollow cylindrical catheter tube 26 is positioned centrally below the beveling mold 12.

FIG. 2 illustrates the second step of the flashless catheter beveling process in which a cylindrical support pin 18, which can be hollow, is inserted into the hollow extruded catheter tube 26 and projects a distance thereabove.

Figure 3:
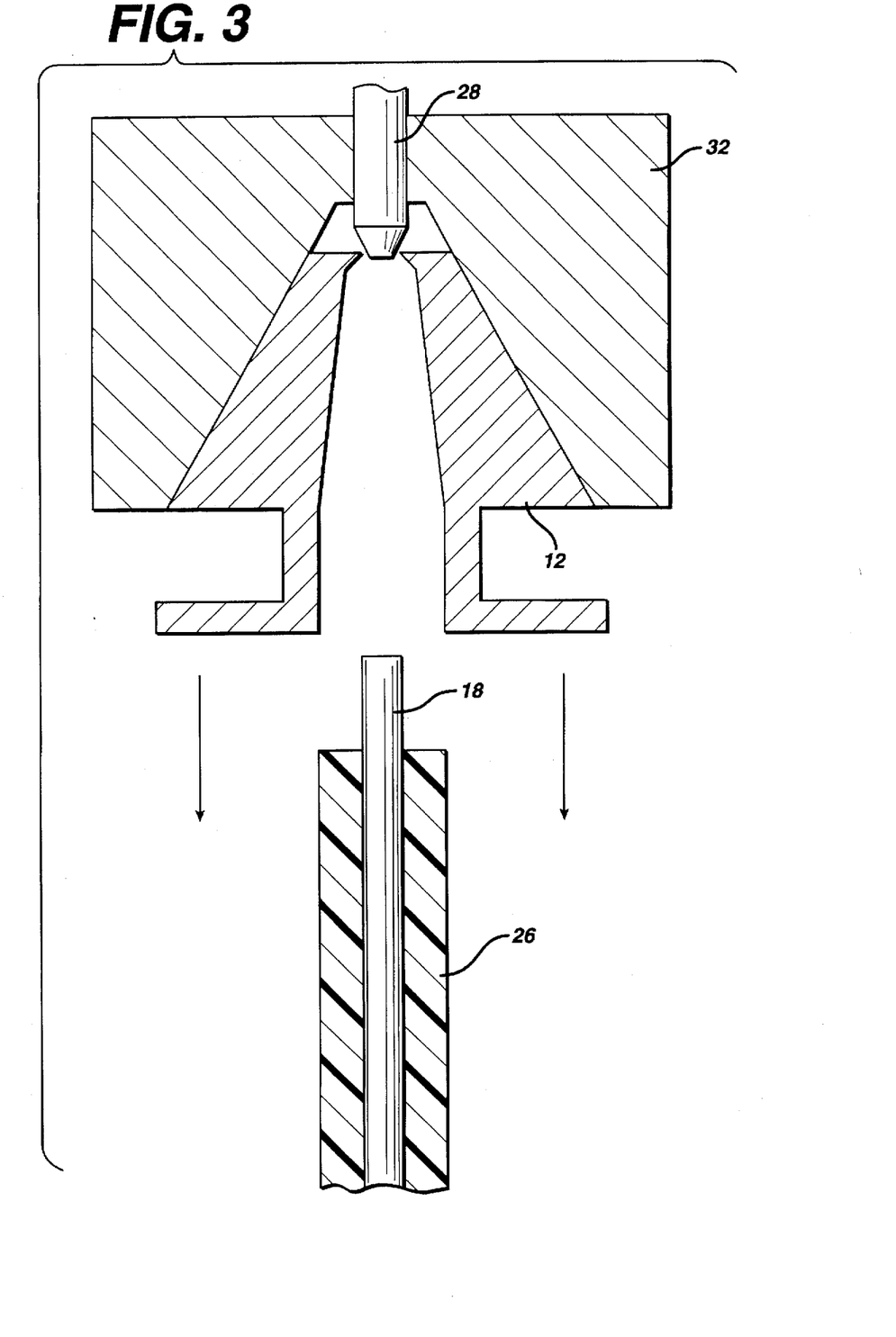
FIG. 3 illustrates the third step of the flashless catheter beveling process in which the beveling mold is moved downwardly at a rapid rate onto the extruded catheter tube positioned on the cylindrical support pin.

FIG. 3 illustrates the third step of the flashless catheter beveling process in which the beveling mold 12 is moved downwardly at an initial fast rate, preferably by a servo control system, onto the extruded catheter tube 18 until the shallow tapered portion 24 of the mold begins to contact the extruded hollow catheter tube 26.

Figure 4:
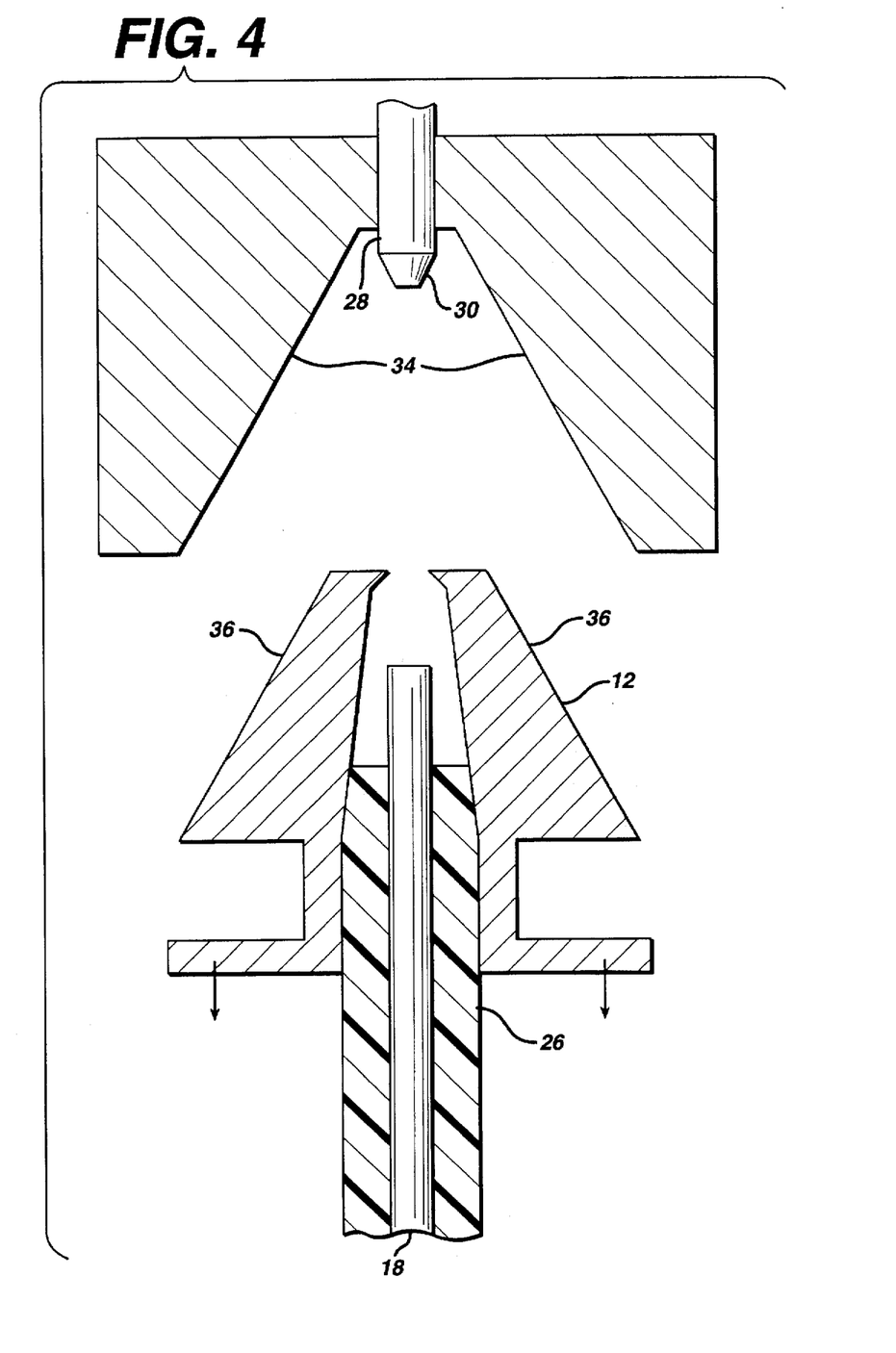
FIG. 4 illustrates the fourth step of the flashless catheter beveling process in which the heated beveling mold is positioned around the extruded catheter tube, and is then moved downwardly at a slower, controlled approach rate, melting the extruded tube to allow it to flow within and assume the shape defined by the interior cavity of the beveling mold.

FIG. 4 illustrates the fourth step of the flashless catheter beveling process in which the heated mold 12 is positioned around the extruded catheter tube 16, and the servo control system lowers the heated mold 12 downwardly onto the extruded catheter tube at a slower, controlled approach rate, melting the exterior surface of the extruded catheter tube to allow it to flow within and assume the shape defined by the interior cavity of the beveling mold.

Figure 5:
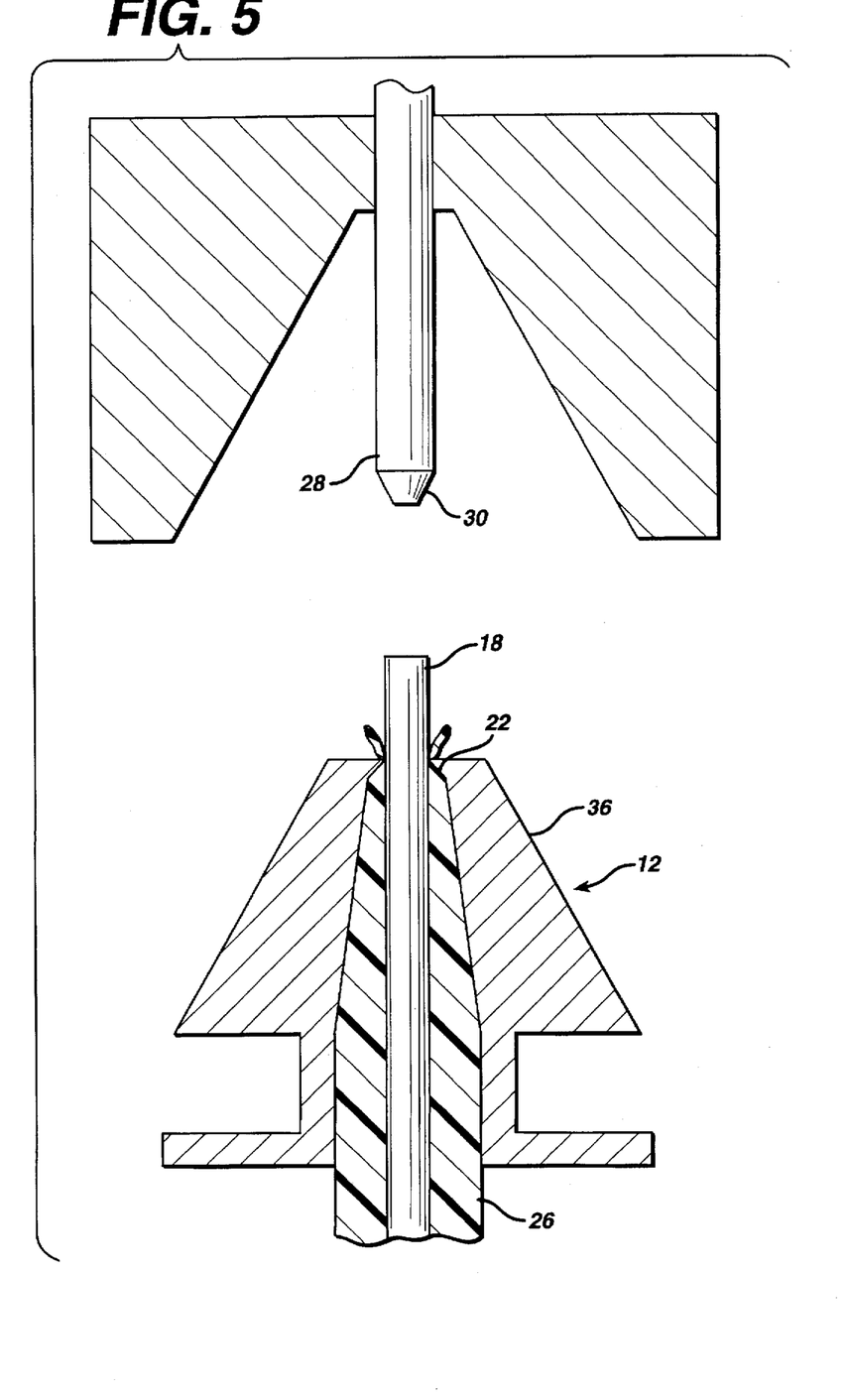
FIG. 5 illustrates the fifth step of the flashless catheter beveling process in which the beveling mold has melted the material of the catheter tube, such that the molten catheter material fills and is shaped by the heated beveling mold, and some of the molten catheter material flashes through the thin annular gap defined between the cylindrical support pin and a circular hole in the top of the beveling mold.

FIG. 5 illustrates the fifth step of the flashless catheter beveling process in which the beveling mold 12 has moved downwardly until the mold pin 18 is positioned within the circular aperture 20, and the material of the catheter tube 16 has been melted and shaped by the heated beveling mold. The downward travel of the heated catheter mold 12 is stopped by the servo control system as the molten catheter material flashes through the thin annular gap defined between the cylindrical support pin 18 and the circular hole 20 in the top of the beveling mold.

Figure 6:
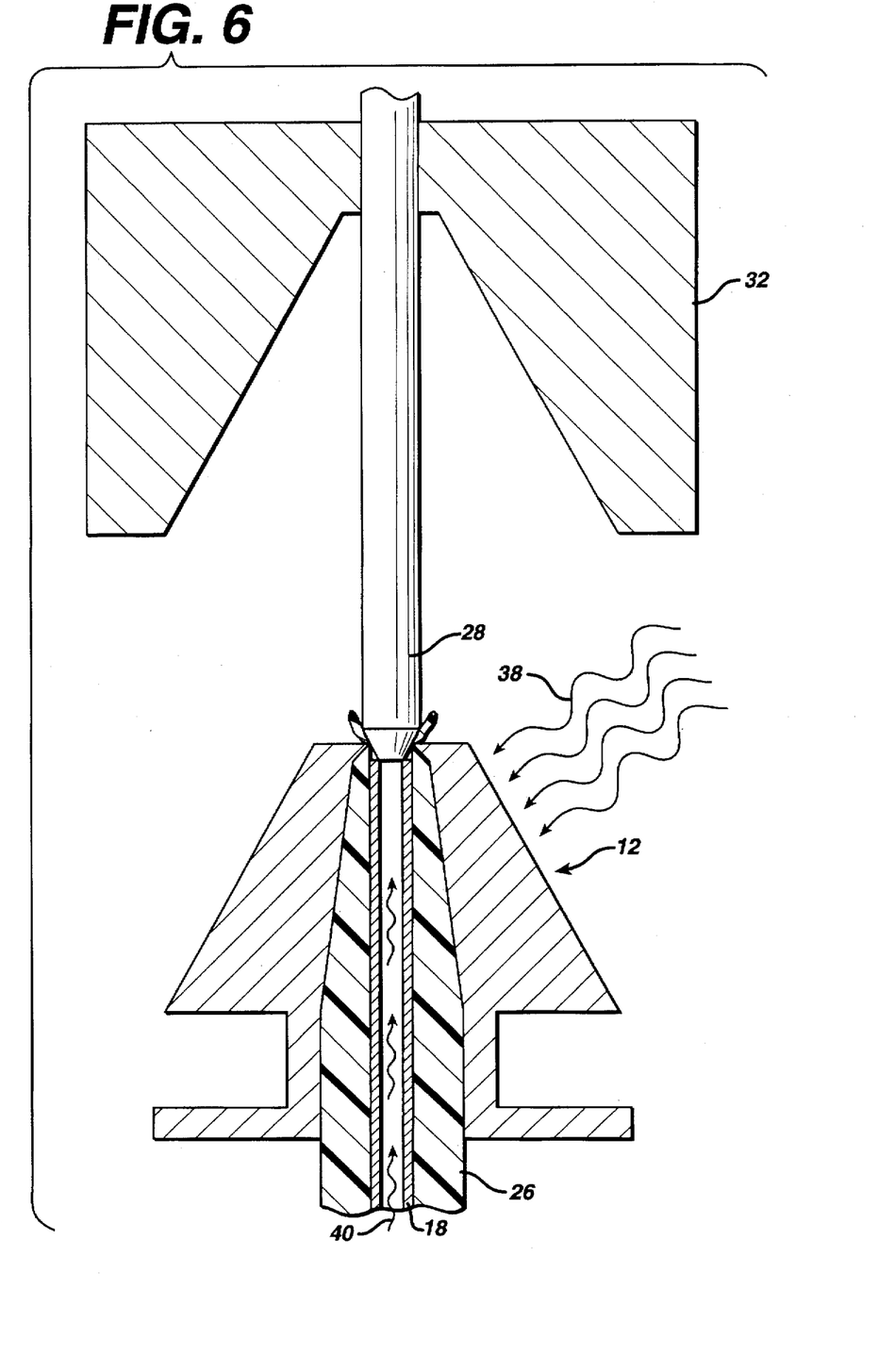
FIG. 6 illustrates the sixth step of the flashless catheter beveling process in which the cylindrical support pin has been withdrawn downwardly and is positioned just below the top surface of the beveling mold, and a top cone pin is lowered into a position in contact with the circular aperture in the top of the beveling mold, such that the flash which has been extruded through the narrow annular gap is pinched off by the beveled surface of the cone pin.

FIG. 6 illustrates the sixth step of the flashless catheter beveling process in which the support pin has been withdrawn downwardly until it is positioned just below the top surface of the beveling mold. The cone pin 28 is then lowered into a position in which the lower beveled surface 30 thereof contacts the edge of the circular aperture 20 in the top of the beveling mold, such that the flash which has been extruded through the narrow annular gap is pinched off by the beveled surface of the cone pin. The cone pin extends slightly into the circular aperture in the mold, and pushes against the interior circular edge of the 27° mold bevel. At this time, the beveling mold 12 is cooled by a directed flow 38 of compressed cooling air which is directed to flow over the frustoconical outer surface 36 of the mold. The cooling air also blows away the pinched off extrudate. In those embodiments wherein the cylindrical support pin 18 is hollow, as illustrated in FIG. 6, a cooling flow 40 of compressed air may also be directed upwardly through the hollow cylindrical through pin.

FIG. 7 illustrates the seventh step of the flashless catheter beveling process in which the cone pin has been withdrawn upwardly, and the catheter mold 12 has been raised back into contact with the temperature controlled heater block 32 to be reheated for the next cycle of operation. The cylindrical support pin 18 is withdrawn downwardly from within the finished and molded catheter 16, and the finished and molded catheter is removed from the molding station. The molding station is then ready for the next cycle of operation as explained herein. FIG. 7 also illustrates the shape of the finished molded catheter which has a precision beveled surface 42 at 27° relative to its longitudinal axis and also has a precision beveled surface 44 at 3° relative to its longitudinal axis.

In different alternative embodiments, the beveled surface 30 of the cone pin could be rounded, curved or tapered with various degrees of steepness. The different movements as described herein are relative movements, and so the extruded catheter tube and support pin might be moved relative to the beveling mold, and likewise for the movement of the cone pin, and the movement of the beveling mold relative to the temperature controlled heater block. Moreover, other forms of heating of the beveling mold might be employed. Likewise, the relative movements might be imparted by moving systems other than a servo control systems. The cone pin might also be positioned not to be in direct contact with the heater block to prevent excessive heating thereof.

While several embodiments and variations of the present invention for a flashless catheter beveling process are described in detail herein, it should be apparent that the disclosure and teachings of the present invention will suggest many alternative designs to those skilled in the art.

What is claimed is:

1. A flashless catheter beveling process comprising:
   a) heating a beveling catheter mold which has an internal cavity which defines an external beveled shape of a catheter and has a circular hole centrally located therein, and wherein in the beveling mold, one end of a distal endmost interior bevel terminates at a surface of the beveling mold, with the distal endmost bevel and the surface of the beveling mold forming an angle at a circular edge of the hole;
   b) inserting a cylindrical support pin into a hollow extruded catheter tube;
   c) positioning the heated beveling mold relative to and around the extruded catheter tube with the cylindrical support pin positioned in the circular hole in the beveling mold, thereby melting the extruded catheter tube to allow molten catheter material to flow within and assume a beveled shape defined by the internal cavity of the beveling mold, the molten catheter material also flashing through a narrow annular gap defined between the cylindrical support pin and the circular hole in the beveling mold;
   d) withdrawing the cylindrical support pin from the circular hole in the beveling mold;
   e) positioning an end of a cone pin in contact with the circular hole in the beveling mold, such that the cone pin contacts the circular edge of the hole formed by the surface of the mold and the distal endmost bevel and pinches off the flash which has been extruded through the narrow annular gap, thereby forming a flashless beveled catheter; and
   f) separating the flashless beveled catheter and the beveling catheter mold and withdrawing the cylindrical pin from within the flashless beveled catheter.

2. A flashless catheter beveling process as claimed in claim 1, wherein the distal endmost bevel and the surface of the beveling mold form an acute angle and a sharp circular edge.

3. A flashless catheter beveling process as claimed in claim 1, wherein the cylindrical support pin is inserted into the hollow catheter tube to project a distance beyond an end of the hollow extruded catheter tube.

4. A flashless catheter beveling process as claimed in claim 1, wherein the beveling mold is heated by being positioned within and contacting a temperature controlled heater block, and the cone pin extends through an aperture in the temperature controlled heater block.

5. A flashless catheter beveling process as claimed in claim 4, wherein the temperature controlled heater block includes an internal frustoconical cavity having the same shape as an external frustoconical surface of the beveling mold to maximize heat flow therebetween.

6. A flashless catheter beveling process as claimed in claim 1, wherein the cylindrical support pin is withdrawn to a position just below the surface of the beveling mold.

7. A flashless catheter beveling process as claimed in claim 1, wherein the distal endmost bevel extends at a bevel angle of 27° with respect to a longitudinal axis of the beveling mold and the flashless beveled catheter.

8. A flashless catheter beveling process as claimed in claim 1, wherein the beveling mold further defines a second interior bevel extending at a bevel angle of 3° with respect to a longitudinal axis of the beveling mold and the flashless beveled catheter.

9. A flashless catheter beveling process as claimed in claim 1, wherein after molding the flashless beveled catheter, the beveling mold is cooled by a flow of air directed across the beveling mold, and the cooling air also blows away pinched off flash extrudate.

10. A flashless catheter beveling process as claimed in claim 1, wherein the cylindrical support pin is hollow, and after molding the flashless beveled catheter a cooling flow of compressed air is directed through the hollow cylindrical support pin.

11. A flashless catheter beveling process as claimed in claim 1, wherein the beveling mold is moved downwardly by a servo control system at a fast rate onto the extruded hollow catheter tube until a shallow tapered portion of the beveling mold begins to contact the extruded hollow catheter tube.

12. A flashless catheter beveling process as claimed in claim 11, wherein after a shallow tapered portion of the beveling mold begins to contact the extruded hollow catheter tube, the servo control system lowers the beveling mold downwardly onto the extruded hollow catheter tube at a slower, controlled approach rate, melting an exterior surface of the extruded hollow catheter tube thereby allowing molten catheter material to flow within and assume a shape defined by the internal cavity of the beveling mold.

13. A flashless catheter beveling process as claimed in claim 12, wherein downward movement of the beveling mold is stopped by the servo control system as the molten catheter material flashes through the narrow annular gap.

* * * * *